United States Patent

Regnat et al.

[11] Patent Number: 5,510,554
[45] Date of Patent: Apr. 23, 1996

[54] PROCESS FOR PREPARING 1,1'-BINAPHTHYLS

[75] Inventors: Dieter Regnat, Frankfurt; Hans-Jerg Kleiner, Kronberg, both of Germany

[73] Assignee: Hoechst Aktiengesellschaft, Germany

[21] Appl. No.: 337,983

[22] Filed: Nov. 14, 1994

[30] Foreign Application Priority Data

Nov. 13, 1993 [DE] Germany .......................... 43 38 826.4

[51] Int. Cl.$^6$ ..................................... C07C 2/84
[52] U.S. Cl. ............................ 585/466; 585/26; 585/411; 585/436; 585/469
[58] Field of Search .............................. 585/26, 411, 436, 585/469, 466

[56] References Cited

U.S. PATENT DOCUMENTS

| | | | |
|---|---|---|---|
| 4,705,895 | 11/1987 | Okano et al. | 564/15 |
| 5,159,093 | 10/1992 | Taketomi et al. | 556/136 |
| 5,347,045 | 9/1994 | Herrmann et al. | 562/35 |

FOREIGN PATENT DOCUMENTS

| | | |
|---|---|---|
| 0326286 | 8/1989 | European Pat. Off. . |
| 62-209040 | 9/1987 | Japan . |
| 1305-039 | 12/1989 | Japan . |

OTHER PUBLICATIONS

Database WPI, Section Ch, Week 9004, Derwent Publications Ltd., AN 90–026705, London, GB, Dec. 8, 1989.
Database WPI, Section Ch, Week 8742, Derwent Publications Ltd., AN 87296427, London, GB; Sep. 14, 1987.

*Primary Examiner*—Anthony McFarlane
*Attorney, Agent, or Firm*—Connolly & Hutz

[57] ABSTRACT

In the preparation of 1,1'-binaphthyls substituted in the 2,2'-positions (and optionally substituted in one or more of positions 3 to 7 and/or 3' to 7'), a 1-halo-2-substituted naphthalene is reacted with a 2-substituted-1-naphthyl-magnesium halide in the presence of a catalyst. The catalyst comprises palladium and a phosphine ligand. Typical phosphine ligands include triphenylphosphine, 1,4-bis(diphenylphosphino)butane, 2,2'-bis(diphenylphosphinomethoxy)-1,1'-binaphthyl, and tetrakis(triphonylphosphine).

21 Claims, No Drawings

PROCESS FOR PREPARING 1,1'-BINAPHTHYLS

The present invention relates to a process for preparing 1,1'-binaphthyls substituted in the 2,2' positions, which may, if desired, carry substituents in one or more of positions 3 to 7 and/or 3' to 7'. Such 1,1'-binaphthyls are building blocks for preparing a number of important compounds which have a variety of applications. Thus, 2,2'-dimethyl-1,1'-binaphthyl (cf. formula A) is an important intermediate in the synthesis of bidentate biarylphosphines. A representative of such a bidentate biarylphosphine, 2,2'-bis(diphenylphosphinomethyl)-1,1'-binaphthyl (="NAPHOS", see formula B) may be mentioned.

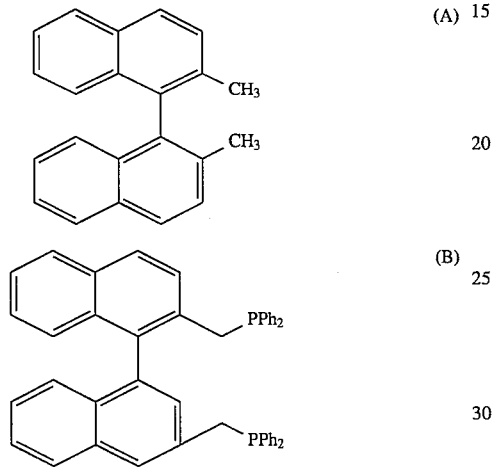

Compounds containing two phosphino groups in the molecule (bidentate phosphine ligands) play an important role in a number of processes in which a transition metal complex is used as a catalyst. Examples of such processes include hydrogenation, hydroformylation and carbonylation reactions.

One way of preparing 1,1'-binaphthyls substituted in the 2,2' positions, which is documented below using 2,2'-dimethyl-1,1'-binaphthyl as an example, is to react 1-bromo-2-methylnaphthalene and 2-methyl-1-naphthyl-magnesium bromide in the presence of a nickel-containing catalyst (nickel-catalyzed aryl coupling) to give 2,2'-dimethyl-1,1'-binaphthyl (see formula A). Since nickel compounds constitute a health risk owing to their carcinogenic properties, they are only suitable for industrial use to a very limited extent. A further, not insignificant disadvantage of this process (M. Kumada et al., Tetrahedron Lett. (1977), 389) is that this the of synthesis only leads to the desired value product in yields of up to 70% when mixtures of various solvents, such as diethyl ether/toluene or diethyl ether/benzene are employed. Owing to the very high volatility and low ignition temperature of diethyl ether, handling such solvent mixtures is problematical. An additional problem arises from the property of diethyl ether to form organic peroxides in an uncontrolled fashion, which may lead to spontaneous explosions.

Furthermore, it is known to prepare various 1,1'-binaphthyls substituted in the 2,2' positions by reacting suitably substituted 1-bromonaphthalenes and 1-naphthylmagnesium bromides in the presence of a palladium-containing catalyst (palladium-catalyzed aryl coupling). (T. Frejd and T. Klingstedt, Acta Chemica Scandinavica 43 (1989) 670). However, when preparing 2,2'-dimethyl-1,1'-binaphthyl, only moderate yields of up to 50% are obtained in diethyl ether/toluene and only very low yields of 13 to 30% are obtained in toluene at 80° C. In this type of synthesis, the palladium catalyst is each time generated in situ from palladium(II) acetyl acetonate and 2,2'-dimethyl-6,6'-bis(diphenylphosphino)biphenyl as diphosphine "BIPHEMP" (cf. formula C) or 2,2'-bis(diphenylphosphino)-1,1'-binaphthyl as diphosphine "BINAP" (cf. formula D). The amount of catalyst used is in each case 1 mol %, relative to 1-bromo-2-methylnaphthalene.

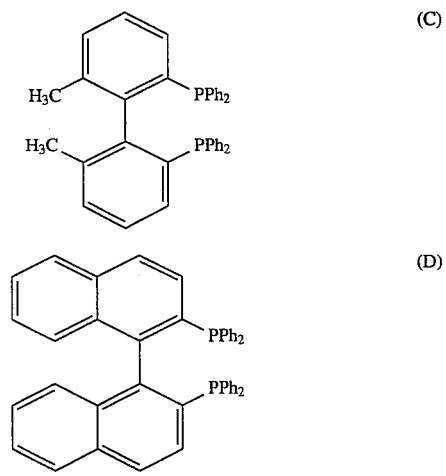

With regard to the prior art processes, it is a reasonable object to develop a process which avoids the disadvantages described above and can be carried out in a simple manner.

This object is surprisingly achieved by a process for preparing 1,1'-binaphthyls. The process comprises reacting a 1-halonaphthalene substituted in the 2 position and, if desired, in one or more of positions 3 to 7 by an alkyl, alkoxy or dialkylamino group having 1 to 6 carbon atoms in the alkyl radical and a 1-naphthylmagnesium halide substituted in the 2 position and, if desired, in one or more of positions 3 to 7 by an alkyl, alkoxy or dialkylamino group having 1 to 6 carbon atoms in the alkyl radical in a nonpolar solvent at 30° to 150° C. in the presence of palladium and a phosphine of the formula

in which X is $(CH_2)_m$ and m is an integer from 1 to 4 or X is a radical

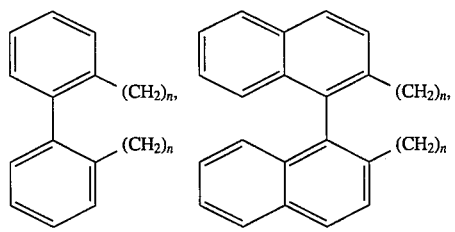

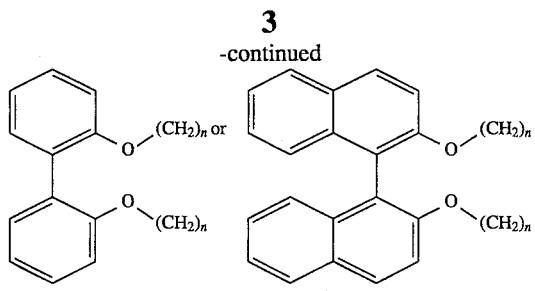

and n is an integer from 0 to 2, each Ar is, independently of the others, a phenyl, tolyl, xylyl, fluorophenyl or trifluoromethylphenyl radical, or in the presence of palladium and a phosphine of the formula

in which R is an alkyl radical having 1 to 6 carbon atoms, a cycloalkyl radical having 5 to 6 carbon atoms or Ar and each Ar has the abovementioned meaning.

When carrying out the process according to the invention, care must be taken that the reaction, in contrast to T. Frejd who obtains the best chemical yields if starting the reaction in diethyl ether, takes place right from the start in a nonpolar solvent which is free even of small amounts of a polar solvent or a mixture of polar solvents.

Accordingly, one advantage of the process according to the invention is that no solvent mixtures have to be used. It is in particular unnecessary to carry out the reaction in the presence of diethyl ether. This eliminates the risks arising from handling diethyl ether.

Accordingly, the process according to the invention can be carried out in a simple and technically safe manner using conventional solvents. A further advantage of the process according to the invention is that the desired value products are available in good yields. In the case of 2,2'-dimethyl-1,1'-binaphthyl, yields of 70% and more can be quite easily obtained.

The process according to the invention has comparatively broad application and leads to 1,1'-binaphthyls substituted in the 2,2' positions and, if desired, in one or more of positions 3 to 7 and/or 3' to 7' by an alkyl, alkoxy or dialkylamino group each having 1 to 6 carbon atoms in the alkyl radical. The reaction proceeds by the following simplified reaction scheme. For the sake of simplicity, the substituents which could be present in positions 3 to 7 or 3' to 7' are not shown.

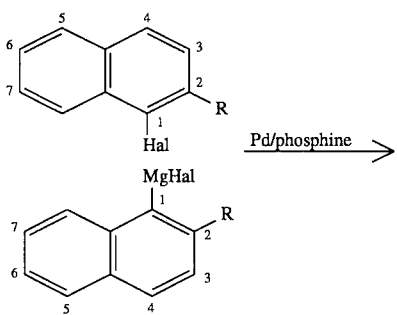

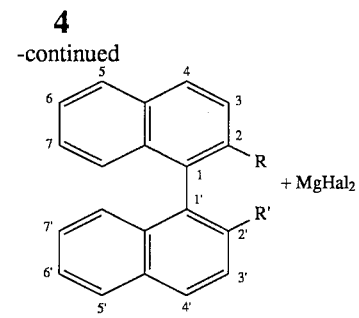

The substituted 1-halonaphthalene used is a 1-halonaphthalene substituted in the 2 position and, if desired, in one or more of positions 3 to 7 by an alkyl, alkoxy or dialkylemino group having 1 to 6 carbon atoms in the alkyl radical. Examples include 1-bromo-2-methylnaphthalene, 1-bromo-2-ethylnaphthalene, 1-bromo- 4-dimethylamino-2-methylnaphthalene and 1-bromo-4-methoxy-2-methylnaphthalene.

Highly suitable substituted 1-halonaphthalenes are 2-alkyl-1-halonaphthalenes each having 1 to 6 carbon atoms in the alkyl radical, in particular 2-methyl-1-halonaphthalene.

The substituted 1-halonaphthalene used is usually a substituted 1-bromonaphthalene or a substituted 1-iodonaphthalene, in particular a substituted 1-bromonaphthalene.

The substituted naphthylmagnesium halide used is a 1-naphthylmagnesiumhalide substituted in the 2 position and, if desired, in one or more of positions 3 to 7 by an alkyl, alkoxy or dialkylamino group each having 1 to 6 carbon atoms in the alkyl radical. These compounds can be prepared by reacting a suitably substituted 1-halonaphthalene with magnesium (Grignard reaction) in which an ether, for example diethyl ether, is usually used as the solvent. After the Grignard reaction is complete, a nonpolar solvent is added to the ether-containing solution, and the ether is then distilled off. This gives an ether-free Grignard reagent. Without claiming to be complete, examples of substituted 1-naphthylmagnesium halides include 2-methyl-1-naphthylmagnesiumbromide, 2-ethyl-1-naphthylmagnesium bromide, 4-dimethylamino-2-methyl-1-naphthylmagnesium bromide and 4-methoxy-2-methyl-1-naphthylmagnesiumbromide.

Highly suitable substituted 1-naphthylmagnesium halides are 2-alkyl-1-naphthylmagnesiumhalides each having 1 to 6 carbon atoms in the alkyl radical, in particular 2-methyl-1-naphthylmagnesium halide.

The substituted 1-naphthylmagnesium halide used is in general a substituted 1-naphthylmagnesium bromide or a substituted 1-naphthylmagnesium iodide, in particular a substituted 1-naphthylmagnesiumbromide.

To carry out the reaction, the substituted 1-halonaphthalene and the substituted 1-naphthylmagnesium halide are reacted in a molar ratio of 1:(0.8 to 1.2), in particular 1:(0.9 to 1.1). In a number of cases, it is sufficient to react the substituted 1-halonaphthalene and the substituted 1-naphthylmagnesium halide in equimolar amounts.

The reaction is carried out in the presence of a nonpolar solvent. Suitable nonpolar solvents are toluene, ethylbenzene, o-xylene, m-xylene, p-xylene, technical-grade mixtures of isomeric xylenes or else mixtures of the abovementioned solvents.

The reaction of the substituted 1-halonaphthalene with the substituted 1-naphthylmagnesium halide can be carried out within a relatively broad temperature range from 30° to 150° C. In a number of cases, it has proven advantageous to carry out the reaction at 50 to 120, in particular 70 to 100, ° C.

The reaction takes place in the presence of palladium. The palladium is usually used in accordance with a substituted 1-halonaphthalene/palladium molar ratio of (500 to 20):1, in particular (200 to 50):1. Suitable forms of palladium are palladium(II) compounds or palladium(0) complexes.

Examples of palladium(II) compounds include palladium(II) acetate, palladium(II) sulfate, palladium(II) nitrate, palladium(II) chloride and/or palladium(II) acetylacetonate. An example of a palladium(0) complex is palladium bis(dibenzylideneacetone).

The reaction is carried out in the presence of a phosphine of the formula (I). Highly suitable phosphines of the formula (I) are those in which m is an integer from 1 to 4, in particular 1 to 2, and n is an integer from 0 to 2 and each Ar, independently of the others, is a phenyl, tolyl or fluorophenyl radical.

Examples of such phosphines of the formula (I) are 1,4-bis(diphenylphosphino)butane, 1,3-bis(diphenylphosphino)propane, 2,2'-bis(diphenylphosphinomethoxy)biphenyl or 2,2'-bis(diphenylphosphinomethoxy)-1,1'-binaphthyl, in particular 1,3-bis(diphenylphosphino)propane, 1,4-bis(diphenylphosphino)butane or 2,2'-bis(diphenylphosphinomethoxy)-1,1'-binaphthyl, preferably 2,2'-bis(diphenylphosphinomethoxy)-1,1'-binaphthyl.

Using a phosphine of the formula (II) instead of a phosphine of the formula (I) also gives good results. Highly suitable phosphines of the formula (II) are those in which R is Ar and Ar is a phenyl, tolyl or fluorophenyl radical. Triphenylphosphine or tri-p-tolylphosphine, in particular triphenylphosphine, are particularly suitable.

Palladium, for example a Pd(II) compound, and the phosphine of the formula (I) are used in a molar ratio of 1:(0.8 to 2.0), in particular 1:(0.9 to 1.5). In most cases, it is sufficient to use palladium and the phosphine of the formula (I) in a molar ratio of 1:1.

If a monophosphine of the formula (II) is used instead of the diphosphine of the formula (I), palladium and the phosphine of the formula (I) are used in a molar ratio of 1:(1.6 to 4.0), in particular 1:(1.8 to 3.0). In most cases, a palladium/phosphine of the formula (II) molar ratio of 1:2 is sufficient.

The process according to the invention can be carried out in a particularly simple manner by using a palladium complex already containing a phosphine of the formula (I) or of the formula (II) instead of palladium and the phosphine. Examples of such palladium compounds include tetrakis(triphenylphosphine) palladium, bis[2,2'-bis(diphenylphosphinomethoxy)-1,1'-binaphthyl]palladium and bis[1,3-bis(diphenylphosphino)propane]palladium.

In general, the reaction is carried out by adding the substituted 1-naphthylmagnesium halide (Grignard compound) to a suspension or solution of substituted 1-halonaphthalene, palladium compound and phosphine of the formula (I) or (II) or palladium(0) complex containing the phosphine of the formula (I) or (II) prepared in a nonpolar solvent. Workup then takes place by hydrolysis with water and dilute acid, in particular dilute mineral acid. The desired value product is recovered by distillation in a high vacuum or by recrystallization, after the solvent has been distilled off.

The examples which follow document the invention without limiting it thereto.

EXPERIMENTAL SECTION

EXAMPLE 1

Preparation of 2-methyl-1,1'-naphthylmagnesium bromide

A solution of 31.0 g (0.14 mol) of 1-bromo-2-methylnaphthalene in 50 ml of anhydrous diethyl ether and 50 ml of anhydrous toluene is added dropwise to a suspension of 3.7 g (0.15 mol) of magnesium filings in 10 ml of anhydrous diethyl ether and 10 ml of anhydrous toluene in the absence of air and moisture. The resulting mixture is refluxed for 6 hours, and the diethyl ether is then distilled off.

EXAMPLE 2

Preparation of 2,2'-dimethyl-1,1'-binaphthyl

2-Methyl-1-naphthylmagnesium bromide prepared according to Example 1 in toluene is added in the absence of air and moisture to a suspension, heated to 70° to 80° C., of 31.0 g (0.14 mol) of 1-bromo-2-methylnaphthalene, 0.0014 mol of the phosphine of the formula (I) [1,4-bis(diphenylphosphino)butane; 2,2'-bis(diphenylphosphinomethoxy)-1,1'-binaphthyl] or 0.0028 mol of the phosphine of the formula (II) (triphenylphosphine) and 0.31 g (0.0014 mol) of palladium(II) acetate in 50 ml of toluene. The mixture is then heated at 80° C. for another hour, cooled to 25° C., and 100 ml of water and 50 ml of 2N hydrochloric acid are added in succession to the reaction mixture. The phases are separated, the aqueous phase is extracted with 50 ml of toluene, and the combined organic phases are concentrated in vacuo. Distillation of the oily, brown residue in a high vacuum gives a pale yellow oil having a boiling point of 175° to 180° C./0.1 to 0.2 mbar. The yields can be found in Table 1 below.

TABLE 1

| Yields according to Example 2 | |
| --- | --- |
| Phosphine ligand of the formula (I) or (II) | Yield [%] |
| Triphenylphosphine | 77 |
| 1,4-Bis(diphenylphosphino)butane | 79 |
| 2,2'-Bis(diphenylphosphinomethoxy)-1,1'-binaphthyl | 80 |

EXAMPLE 3

Preparation of 2,2'-dimethyl-1,1'-binaphthyl

2-Methyl-1-naphthylmagnesiumbromide in toluene prepared according to Example 1 is added in the absence of air and moisture to a solution, heated to 70° to 80° C., of 31.0 g (0.14 mol) of 1-bromo-2-methylnaphthalene and 1.6 g (0.0014 mol) of tetrakis(triphenylphosphine)palladium(0) in 50 ml of toluene. The mixture is then heated at 80° C. for another hour, cooled to 25° C., and 100 ml of water and 50 ml of 2N hydrochloric acid are added in succession to the reaction mixture. The phases are separated, the aqueous phase is extracted with 50 ml of xylene and the combined organic phases are concentrated in vacuo. Distillation of the oily, brown residue in a high vacuum gives 30.8 g (78%) of pale yellow, viscous oil having a boiling point of 175° to 180° C./0.1 to 0.2 mbar.

What is claimed is:

1. A process for preparing 1,1'-binaphthyls, which comprises reacting a 1-halonaphthalene substituted in the 2 position and, optionally, in one or more of positions 3 to 7 by an alkyl, alkoxy or dialkylamino group having 1 to 6 carbon atoms in the alkyl radical and a 1-naphthylmagnesiumhalide substituted in the 2 position and, optionally, in one or more of positions 3 to 7 by an alkyl, alkoxy or dialkylamino group having 1 to 6 carbon atoms in the alkyl radical in a nonpolar solvent at 30° to 150° C. in the presence of palladium and a phosphine of the formula

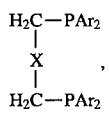   (I)

in which X is $(CH_2)_m$ and m is an integer from 1 to 4 or X is a radical

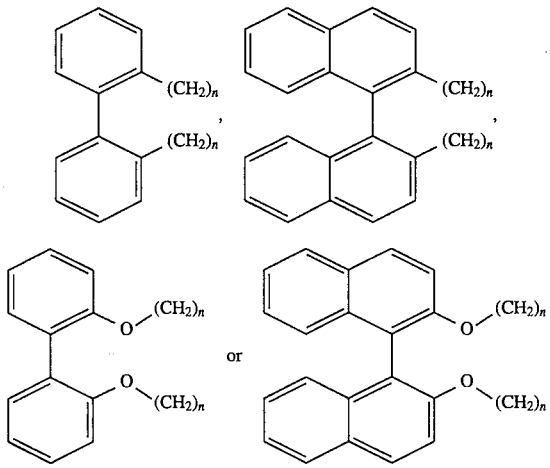

and n is an integer from 0 to 2, each Ar is, independently of the others, a phenyl, tolyl, xylyl, fluorophenyl or trifluoromethylphenyl radical, or in the presence of palladium and a phosphine of the formula

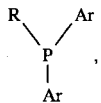   (II)

in which R is an alkyl radical having 1 to 6 carbon atoms, a cycloalkyl radical having 5 to 6 carbon atoms or Ar and each Ar has the abovementioned meaning.

2. The process as claimed in claim 1, wherein the substituted 1-halonaphthalene used is a 2-alkyl-1-halonaphthalene having 1 to 6 carbon atoms in the alkyl radical.

3. The process as claimed in claim 1, wherein the substituted 1-halonaphthalene used is a 2-methyl-1-halonaphthalene.

4. The process as claimed in claim 1, wherein the substituted 1-halonaphthalene used is a substituted 1-bromonaphthalene or 1-iodonaphthalene.

5. The process as claimed in claim 1, wherein the substituted 1-naphthylmagnesium halide used is a 2-alkyl-1-naphthylmagnesiumhalide having 1 to 6 carbon atoms in the alkyl radical.

6. The process as claimed in claim 1, wherein the substituted 1-naphthylmagnesium halide used is a 2-methyl-1-naphthalenemagnesium halide.

7. The process as claimed in claim 1, wherein the substituted 1-naphthylmagnesium halide used is a substituted 1-naphthylmagnesium bromide or 1-naphthylmagnesium iodide.

8. The process as claimed in claim 1, wherein the substituted 1-halonaphthalene and the substituted 1-naphthylmagnesium halide are reacted in a molar ratio of 1:(0.8 to 1.2).

9. The process as claimed in claim 1, wherein the nonpolar solvent used is toluene, ethylbenzene, o-xylene, m-xylene, p-xylene, technical-grade mixtures of isomeric xylenes or mixtures thereof.

10. The process as claimed in claim 1, wherein the reacting step is carried out at 50 to 120.

11. The process as claimed in claim 1, wherein the palladium is used in accordance with a substituted 1-halonaphthalene/palladium molar ratio of (500 to 20):1.

12. The process as claimed in claim 1, wherein the palladium used is a Pd(II) compound.

13. The process as claimed in claim 12, wherein the Pd (II) compound used is Pd(II) acetate, Pd(II) sulfate, Pd(II) nitrate, Pd(II) chloride, or Pd(II) acetylacetonate.

14. The process as claimed in claim 1, wherein a phosphine of the formula (I) in which m is an integer from 1 to 4, and n is an integer from 0 to 2 is used.

15. The process as claimed in claim 1, wherein a phosphine of the formula (I) in which each Ar, independently of the others, is a phenyl, tolyl or fluorophenyl radical is used.

16. The process as claimed in claim 1, wherein the phosphine of the formula (I) used is 1,4-bis(diphenylphosphino)butane, 1,3-bis(diphenylphosphino) propane, 2,2'-bis-(diphenylphosphinomethoxy)biphenyl or 2,2'-bis(diphenylphosphinomethoxy)-1,1'-binaphthyl, in particular 2,2'-bis(diphenylphosphinomethoxy)-1,1'-binaphthyl.

17. The process as claimed in claim 1, wherein a phosphine of the formula (II) in which R is Ar and Ar is a phenyl, tolyl or fluorophenyl radical is used.

18. The process as claimed in claim 1, wherein the phosphine of the formula (II) used is triphenylphosphine or tri-p-tolylphosphine.

19. The process as claimed in claim 1, wherein palladium and the phosphine of the formula (I) are used in a molar ratio of 1:(0.8 to 2.0) or palladium and phosphine of the formula (II) are used in a molar ratio of 1:(1.6 to 4.0).

20. The process as claimed in claim 1, wherein palladium and the phosphine of the formula (I) or (II) are used in the form of a palladium complex containing the phosphine of the formula (I) or (II).

21. The process as claimed in claim 1, wherein palladium and the phosphine of the formula (I) or (II) are used in the form of bis[1,3-bis(diphenylphosphino)propane]palladium, bis[2,2'-bis(diphenylphosphinomethoxy)-1,1'-binaphthyl]palladium or tetrakis (triphenylphosphine) palladium.

* * * * *